United States Patent
Narayan et al.

(10) Patent No.: US 11,332,696 B2
(45) Date of Patent: May 17, 2022

(54) 2-ETHYLHEXANOL ETHOXYLATE AS A HYDROTROPE IN LIQUID DETERGENTS

(71) Applicant: SABIC GLOBAL TECHNOLOGIES B.V., Bergen op Zoom (NL)

(72) Inventors: Karumanassery Chidambara Iyer Narayan, Riyadh (SA); Flaiyh Farhan N. Al-Anazi, Riyadh (SA); Mohammed S. Bakalla, Riyadh (SA); Qasem Ahmed A. Ghazwani, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 328 days.

(21) Appl. No.: 16/338,724

(22) PCT Filed: Oct. 30, 2017

(86) PCT No.: PCT/IB2017/056735
§ 371 (c)(1),
(2) Date: Apr. 2, 2019

(87) PCT Pub. No.: WO2018/078601
PCT Pub. Date: May 3, 2018

(65) Prior Publication Data
US 2021/0032569 A1     Feb. 4, 2021

Related U.S. Application Data

(60) Provisional application No. 62/415,077, filed on Oct. 31, 2016.

(51) Int. Cl.

| | | |
|---|---|---|
| *C11D 1/22* | (2006.01) | |
| *C11D 1/831* | (2006.01) | |
| *C11D 3/04* | (2006.01) | |
| *C11D 11/04* | (2006.01) | |
| *C07C 303/28* | (2006.01) | |
| *C07C 309/63* | (2006.01) | |

(52) U.S. Cl.
CPC ............ *C11D 1/831* (2013.01); *C07C 303/28* (2013.01); *C11D 1/22* (2013.01); *C11D 3/044* (2013.01); *C11D 11/04* (2013.01); *C07C 309/63* (2013.01)

(58) Field of Classification Search
None
See application file for complete search history.

(56) References Cited

U.S. PATENT DOCUMENTS

| | | | | |
|---|---|---|---|---|
| 5,385,681 A * | 1/1995 | Sato | ................. | C11D 10/042 510/355 |
| 5,468,423 A | 11/1995 | Garabedian, Jr. et al. | | |
| 5,736,498 A | 4/1998 | Gray | | |
| 6,162,778 A | 12/2000 | McKillop et al. | | |
| 6,387,868 B1 | 5/2002 | Uno et al. | | |
| 6,537,960 B1 | 3/2003 | Ruhr et al. | | |
| 2002/0086805 A1 | 7/2002 | Genova et al. | | |
| 2008/0221006 A1 * | 9/2008 | Heisig | .................. | C11D 3/33 510/272 |
| 2008/0267900 A1 * | 10/2008 | Steinbrenner | ........... | C23C 16/44 424/76.1 |
| 2013/0121944 A1 * | 5/2013 | Leyrer | ................. | A61K 8/8158 424/70.16 |
| 2013/0313154 A1 * | 11/2013 | Hernandez | ........... | C11D 17/043 206/524.7 |
| 2016/0177224 A1 * | 6/2016 | Braeckman | .............. | C11D 1/14 510/237 |

FOREIGN PATENT DOCUMENTS

| | | |
|---|---|---|
| CN | 1248283 | 3/2000 |
| CN | 1067103 | 6/2001 |
| WO | WO 02/086041 A1 * | 10/2002 |
| WO | 2014095793 A1 | 6/2014 |
| WO | 2014177321 A1 | 11/2014 |

OTHER PUBLICATIONS

International Preliminary Report on Patentability for International Application No. PCT/IB2017/056735, International Filing Date Oct. 30, 2017, dated Jan. 3, 2019, 15 pages.
International Search Report for International Application No. PCT/IB2017/056735, International Filing Date Oct. 30, 2017, dated Jan. 18, 2018, 5 pages.
Written Opinion for International Application No. PCT/IB2017/056735, International Filing Date Oct. 30, 2017, dated Jan. 18, 2018, 6 pages.
Chinese Office Action for the corresponding Chinese Application No. 2017800675668; Date of Filing: Oct. 30, 2017; dated Apr. 23, 2020; English translation, 14 pages.
Liu et al., "Dyeing agent" Textile Industry Press 1991, p. 253 (No English Translation provided).
Office Action issued in Corresponding Chinese Application No. 201780067566.8, dated Jun. 21, 2021 (No English Translation provided).
Weng et al., "Application of non-ionic surfactants" China Light Industry Press 1983, p. 16 (No English Translation provided).
Yuan, Junxiang. "Industrial detergent and washing effects" Hunan Science & Technology Press 1993, 223-225 (No English Translation provided).
Zheng et al., "Manufacturing technology of synthetic detergent" China Light Industry Press 1996, p. 339 (No English Translation provided).

* cited by examiner

*Primary Examiner* — Lorna M Douyon
(74) *Attorney, Agent, or Firm* — Norton Rose Fulbright US LLP

(57) ABSTRACT

The present disclosure relates to a detergent composition including an alkyl benzyl sulfonate surfactant and ethoxylated 2-ethylhexanol. The composition may be formed by neutralizing a alkylbenzene sulfonic acid with an alkaline solution in the presence of a hydrotrope.

12 Claims, No Drawings

2-ETHYLHEXANOL ETHOXYLATE AS A HYDROTROPE IN LIQUID DETERGENTS

CROSS REFERENCE TO RELATED APPLICATIONS

This application is a 371 of International Application No. PCT/IB2017/056735, filed Oct. 30, 2017, which is incorporated by reference in its entirety, and which claims priority to U.S. No. 62/415,077 filed Oct. 31, 2016.

TECHNICAL FIELD

The disclosure concerns methods of forming aqueous alkyl benzene sulfonate compositions.

BACKGROUND

For efficient laundering of fabrics or cleansing of surfaces, detergent compositions generally include a variety of active ingredients, such as one or more anionic surfactants combined with a nonionic surfactant and detergent builder materials such as alkali metal carbonates and zeolites. Detergent compositions may further comprise additives such as electrolytes and adjuvants including brighteners, perfumes and colorants. Solvent-free detergents have been prepared from linear alkyl benzene sulfonate anionic surfactants. Such solid detergents often require very good dispensing and dissolution profiles to ensure cleaning performance. With liquid-based detergents, it is important that the detergent components be soluble or dispersed throughout, and that the liquid detergent product be primarily stable and pourable. However, the processes of preparing certain detergent compositions may result in systems exhibiting limited solubility of the ingredients in water and/or a highly viscosity liquid that is difficult to pour. Accordingly, there remains a need in the art for methods of forming surfactant compositions that efficiently cleanse soiled or stained surfaces and fabrics while the compositions maintain rheological and physical properties amenable for use as a fluid detergent composition.

SUMMARY

The present disclosure relates to a method including: forming an alkaline solution; combining the alkaline solution with a portion of ethoxylated 2-ethylhexanol to provide an aqueous solution; and slowly adding linear alkyl benzene sulfonic acid to the aqueous solution to provide an linear alkyl benzene sulfonate solution. The ethoxylated 2-ethylhexanol includes 7 moles ethylene oxide units, and the linear alkyl benzene sulfonate solution exhibits a viscosity that is at least about 40% less than the viscosity of substantially similar solution. The substantially similar solution includes the alkaline solution and the linear alkyl benzene sulfonic acid in the absence of the ethoxylated 2-ethylhexanol. The linear alkyl benzene sulfonate solution exhibits values for surface tension and foaming properties within about 5% of the values for surface tension and foaming of the substantially similar solution in the absence of the ethoxylated 2-ethylhexanol.

While aspects of the present disclosure may be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional aspects of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Linear alkyl benzene sulfonate (LABS) surfactants are a common anionic detersive (detergent) surfactant. Exemplary uses of LABS include surfactants, or surfactant intermediates, as well as components in wetting, dispersing and cleaning agents, and as components in emulsifiers, polymerization processes, and crop protection agents. In liquid detergent manufacture, the LABS surfactant may be formed by the neutralization of a linear alkyl benzene sulfonic acid with an appropriately alkaline solution. The neutralization process however may result in a very viscous, minimally pourable solution or slurry. Simply adding water may resolve the flow problems, but the active components are simultaneously diluted. To reduce viscosity, a hydrotrope may be added. Conventionally the hydrotrope typically comprises cumene sulfonates. Cumene sulfonates, among many other hydrotropes, do not exhibit detergent or cleansing properties and thus do not contribute to the effectiveness of the LABS surfactant. The compositions and methods of the present disclosure provide a LABS surfactant formed by neutralizing linear alkyl benzene sulfonic acid with an alkaline solution comprising ethoxylated 2-ethylhexanol as a hydrotrope.

Described as active surface agents, surfactants are the primary components of detergents and other cleansing compositions. Surfactants comprise amphiphilic molecules as they include both hydrophilic and hydrophobic portions to aid in cleansing. When in contact with stains or soils in solution, the hydrophilic, nonpolar region of the surfactant is attracted to water, and the lipophilic (or hydrophobic) region is attracted to the oil of the stain or soil. With agitation, the surfactant molecules surround the oil globules, forming micelles, which can then be dislodged from a substrate. The most popular synthetic detergents include linear alkyl benzene sulfonates, alpha olefin sulfonates, and primary alkyl sulfates which belong to the class of anionic surfactants. Surfactants of the non-ionic, cationic, amphoteric and zwitterionic character are also known. Anionic surfactants, such as LABS, comprise an overall negative surface charge such that the molecule dissociates to negative ions in solution, have been widely employed as the primary cleansing agent in detergent compositions. Nonionic surfactants and anionic surfactants are often combined to form robust and efficient detergent compositions. Nonionic surfactants that are alkylene oxide adducts of alcohols, also referred to as alkoxylated alcohols or alcohol alkoxylates, are known to be good wetting agents, and are often present in compositions for the cleaning of hard surfaces. Still, many alcohol alkoxylates are not soluble enough in aqueous solutions, and therefore need the presence of a hydrotrope to improve their solubility.

In addition to the anionic and nonionic surfactants, detergent compositions may also contain a number of other enhancing components including detergent builders, polycarboxylates, optical brighteners, alkaline sources, anti-redeposition agents, pH modifiers, emulsifiers, and viscosity modifiers.

The anionic surfactant may complex with free cations, such as calcium and magnesium cations, that may be present in washing solutions which may cause the anionic surfactant to precipitate out of solution thereby reducing detergent efficiency. Hydrotropes are also useful in such detergent compositions to render the active detergent components water-soluble and the composition more homogeneous. Conventional hydrotropes generally include MPG (mono-propylene glycol), glycerol, sodium cumene sulfonate, ethanol, other glycols, e.g. di propylene glycol, di-ethers and urea. As provided above however, conventional hydrotropes typically may not contribute to overall detergency. According to aspects of the present disclosure, a robust detergent composition may be formed by combining an alkaline solution with an ethoxylated alcohol as a hydrotrope to neutralize a linear alkyl benzene sulfonic acid.

The compositions prepared herein may exhibit improved properties of detergency and anti-redeposition. The compositions may be formed by neutralizing linear alkyl benzene sulfonic acid with an alkaline solution comprising an ethoxylated alcohol. More specifically, the linear alkyl benzene sulfonic acid may be neutralized with an alkaline solution comprising an ethoxylated 2-hexylalcohol having seven ethylene oxide units. The alkaline solution may be prepared by dissolving an alkali metal hydroxide, such as sodium hydroxide, in water. The ethoxylated 2-hexanol may act as a hydrotrope and is thereby configured to reduce viscosity of the resultant solution. Further, the ethoxylated 2-hexanol may function as a non-ionic surfactant thus contributing to the overall detergency of the resultant surfactant solution.

In some aspects, an alkaline solution may be prepared for neutralization of a linear alkyl benzene sulfonic acid. The alkaline solution may be formed using an alkaline source. Exemplary sources of alkalinity include alkali metal hydroxides and alkaline earth metal hydroxides, metal and alkali earth metal salts of, for example, carbonate, phosphate, silicate, layered silicate, hydroxide, and mixtures thereof. Exemplary alkali metal hydroxides include, for example, sodium or potassium hydroxide. Suitable alkaline earth metal hydroxides include, for example, magnesium hydroxide. An alkali or alkaline earth metal hydroxide may be used to form an alkaline solution to neutralize the linear alkyl benzene sulfonic acid. In some aspects, the alkaline solution may be prepared in an amount that is at least a stoichiometric molar ratio sufficient to completely neutralize the linear alkyl benzene sulfonic acid. In further aspects, the alkaline solution is prepared in an amount so as to be in stoichiometric excess with the linear alkyl benzene sulfonic acid. The stoichiometric molar ratio of alkaline solution to linear alkyl benzene sulfonic acid may be from 1.1 to 1.1:1 or from about 1:1 to about 1.1:1. In a specific example, the stoichiometric molar ratio of alkaline solution to LABS acid may be 1:1 or about 1:1. In a further example, the stoichiometric molar ratio may be 1.2:1 or about 1.2:1. In an aspect, the alkaline solution may be prepared at a strength or concentration of 12.5% or about 12.5%. In further aspects, the alkaline solution may be prepared to be within a pH range of 7-8.

The alkaline solution may be formed in an appropriate container or vessel, the size of which may depend upon the scale at which the composition is prepared. The alkaline solution may be formed according to a number of methods well known in the art. In an aspect, the alkaline solution may be formed by the dissolution of an alkali metal hydroxide in water. For example, sodium hydroxide may be dissolved in a portion of water to provide a caustic soda (or sodium hydroxide) solution.

Upon forming the alkaline solution, a portion of ethoxylated 2-ethylhexanol may be added thereto and the resulting aqueous solution mixed well. The alkaline solution may be combined with a portion of ethoxylated 2-ethylhexanol. In the surfactant composition prepared according to the methods disclosed herein, the ethoxylated 2-ethylhexanol belongs to a class of alkoxylated alcohols. These alkoxylated alcohols typically represent non-ionic surfactant materials. As provided herein, the alkoxylated alcohol ethoxylated 2-ethylhexanol may perform as a hydrotrope thereby reducing the viscosity and increasing solubility of the composition formed herein upon the addition of the linear alkyl benzene sulfonic acid. The ethoxylated 2-ethylhexanol comprises 7 moles of ethylene oxide units. The ethoxylated 2-ethylhexanol may be added to the sodium hydroxide solution.

Ethoxylated 2-ethylhexanol represents an ethyoxylated alcohol, also described as an alkylene (ethylene) oxide adduct of an alcohol. Generally, an ethoxylated alcohol has a structure according to formula (1).

(1)

wherein R comprises a hydrocarbyl or alkyl moiety and wherein n is corresponds to the number of moles of ethylene oxide (or ethyleneoxy, EO) present per mole of alcohol. The EO units may correspond to the hydrophilic or water soluble portions of the surfactant molecule. In some aspects, n may be from 1 to 100, or from about 1 to about 100. In further examples, n is from 1 to 10, or from about 10. Wherever a degree of alkoxylation (or ethoxylation) is discussed the numbers referred to are molar average numbers, essentially corresponding to the reaction of the indicated number of moles of alkylene (or ethylene) oxide with one more of alcohol.

As provided herein, a portion of ethoxylated 2-ethylhexanol may be added to the alkaline solution prepared according to the present disclosure. An ethoxylated 2-ethylhexanol may be represented as formula 2.

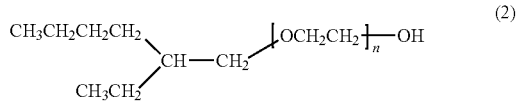

(2)

In one aspect, the ethoxylated 2-ethylhexanol may comprise a number of EO units or moles of EO. The ethoxylated 2-ethylhexanol may comprise from about 1 to about 10 moles or units of EO per molecule. For example, the ethoxylated 2-ethylhexanol may comprise 7 EO units. An ethoxylated 2-ethylhexanol comprising 7 EO units may be represented as formula 2, wherein n is 7.

The ethoxylated alcohol provided herein may function as a hydrotrope and as nonionic surfactant. With respect to the molecule as a surfactant, the hydrocarbyl or alkyl moiety R as in formula 1 and the 2 may correspond to a hydrophobic/lipophilic portion of the surfactant. The EO units may correspond to the hydrophilic or water soluble portions of the surfactant molecule.

In various aspects of the present disclosure, the composition may comprise an ethoxylated alcohol as a hydrotrope. A hydrotrope may be defined as a compound that solubilizes hydrophobic compounds in aqueous solutions. More specifically, the hydrotrope may be a compound that improves the solubility of surfactants in water. Hydrotropes are sometimes also called e.g. solubilizers, couplers, compatibility agents or co-surfactants.

Often, the hydrotrope may be also be a good wetting agent but a good hydrotrope is not necessarily a good wetting agent. (reduces the surface tension of water or another liquid, causing the liquid to spread across or penetrate more easily the surface of a solid reduces the surface tension of water or another liquid, causing the liquid to spread across or penetrate more easily the surface of a solid Its main task is to enhance the solubility of the surfactant, and thereby increase the wetting ability of the composition.

In certain aspects of the present disclosure, the ethoxylated alcohol may be substituted with a propoxylated alcohol. That is, the alcohol may comprise one or more units of propylene oxide ($-OCH_2CH_2CH_2-$) in lieu of ethylene oxide. A propoxylated alcohol may thus also be used as the hydrotrope disclosed herein and combined with the alkaline solution.

The ethoxylated 2-ethylhexanol may be added to the alkaline solution in an amount of 0.05 wt. % or about 0.5 wt. %.

As provided herein, the ethoxylated 2-ethylhexanol may be added to the alkaline solution to form an aqueous solution for neutralization of a linear alkyl benzene sulfonic acid. A linear alkyl benzene sulfonic acid may be defined by formula (3).

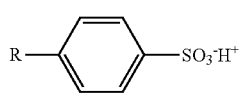

(3)

where R comprises a straight chain hydrocarbyl or alkyl moiety. The chain length distribution may generally range from C8 to C20. The linear alkyl benzene sulfonic acid can be any linear alkyl benzene sulfonic acid, for example a $C_{10-13}$ alkyl benzene sulfonic acid. In a specific example, the linear alkyl benzene sulfonic acid may have a C12 chain length.

The linear alkyl benzene sulfonic acid may be added to the aqueous solution in a molar ratio of 1:1 or about 1:1.

As used herein, the term "alkyl" means a hydrocarbyl moiety which is straight or branched, saturated or unsaturated. Unless otherwise specified, alkyl moieties are preferably saturated or unsaturated with double bonds, preferably with fewer than two double bonds. Included in the term "alkyl" is the alkyl portion of acyl groups.

The linear alkyl benzene sulfonic acid may be neutralized with the aqueous solution prepared according to the methods described herein to produce the corresponding alkaline salt (e.g., the sodium salt) of the linear alkyl benzene sulfonic acid. Neutralization of the linear alkyl benzene sulfonic acid with the prepared aqueous solution provides a detergent solution exhibiting improved detergency and anti-redeposition properties.

According to the methods disclosed herein, an alkaline solution may first be formed. The alkaline solution may be prepared by dissolving sodium hydroxide in a portion of water. The sodium hydroxide solution may be formed so as to neutralize an addition of the acid form of anionic surfactant LABS.

In certain aspects, the alkaline solution may be formed from sodium hydroxide. A portion of solid sodium hydroxide may be dissolved in water to form a sodium hydroxide solution. In a further example, a sodium hydroxide solution may be obtained commercially. Where sodium hydroxide is dissolved in a portion of water, the dissolution may be performed in an appropriate vessel under stirring to provide a homogenous alkaline solution. In further aspects, potassium hydroxide may be used to form a potassium hydroxide solution. The term "homogenous alkaline solution" may be defined as a reaction equilibrium in which a single phase exists. Thus, there exists a reaction equilibrium in which the reactants, and products are all or substantially all in the same phase (e.g., the reactants and products are fully dissolved or substantially dissolved in the basic aqueous solution).

The alkaline solution may then be combined with a suitable amount of ethoxylated 2-ethylhexanol. A portion of ethoxylated 2-ethylhexanol 7EO may be added to the alkaline solution (e.g., sodium hydroxide solution). The ethoxylated alcohol may be added to the alkaline solution under stirring to provide a homogenous aqueous solution.

A portion of linear alkyl benzene sulfonic acid may be added gradually to the aqueous solution thereby neutralizing the linear alkyl benzene sulfonic acid and providing an alkali linear alkyl benzene sulfonate solution. Addition of the linear alkyl benzene solution may be added gradually or slowly. A slow or gradual addition of the acid to the aqueous solution may require that the portion of linear alkyl benzene sulfonic acid that is added is divided into smaller portions. Each smaller portion may be introduced to the aqueous solution under stirring. As an example, smaller portions may be smaller volumetric portions or smaller weight portions. The smaller portions may be added individually under stirring to the aqueous solution.

To form the linear alkyl benzene sulfonate solution, the linear alkyl benzene acid may be added slowly to the prepared aqueous solution to form a slurry. The linear alkyl benzene sulfonic acid may be added in smaller sub-portions while the aqueous solution is stirred or agitated so as to mix the contents of the solution. The adding of the linear alkyl sulfonic acid may occur within a mixer or an apparatus which suitably homogenizes the slurry. Neutralization of the linear alkyl benzene sulfonic acid forms a water-soluble salt of the linear alkyl benzene sulfonate surfactant described herein.

Neutralization of the linear alkyl benzene sulfonic acid by combining with the alkaline solution comprising the ethoxylated 2-ethylhexanol (i.e., the aqueous solution) may take place in any appropriate container, but is preferably conducted in a mixer or a vessel equipped with mixing or agitation mechanism. Slowly adding the linear alkyl benzene sulfonic acid to the aqueous solution comprising the alkaline solution and the ethoxylated 2-ethylhexanol may homogenize the linear alkyl benzene acid with the alkaline material to form the linear alkyl benzene sulfonate solution of the present disclosure.

By neutralizing the linear alkyl benzene sulfonic acid with the alkaline and ethoxylated alcohol solution described herein, the resulting linear alkyl benzene sulfonate solution may exhibit an improved viscosity while maintaining surface tension and foaming properties of a substantially similar solution in the absence of the ethoxylated 2-ethylhexanol. Specifically, the linear alkyl benzene sulfonate solution may exhibit a viscosity that is at least 40% or about 40% less than the viscosity of substantially similar solution, wherein the substantially similar solution comprises the alkaline solution and linear alkyl benzene sulfonic acid in the absence of the ethoxylated 2-ethylhexanol. Further, the resulting linear alkyl benzene sulfonate solution may exhibit values for surface tension and foaming properties within about 5% of the values for surface tension and foaming of the substantially similar solution in the absence of the ethoxylated 2-ethylhexanol. Thus, unlike the substantially similar solution, the linear alkyl benzene sulfonate solution may exhibit a pourable quality (i.e., lower viscosity) while maintaining its physical properties (i.e., surface tension, foaming).

In further aspects, the linear alkyl benzene sulfonate solution may exhibit certain detergent and anti-redeposition properties. Performance as a detergent may be evaluated according to the principle that a deposit of material or a stain on a fabric would result in a lower reflectance of light observed at the fabric. In turn, the removal of such a deposit would increase the reflectance of light observed at the fabric. Thus, the higher the reflection of light, the greater the extent to which the stain has been removed and the better detergent performance of the composition. In some examples, the linear alkyl benzene sulfonate solution described herein may exhibit improved detergent and anti-redeposition properties when compared to a substantially similar solution formed by neutralizing linear alkyl benzene sulfonic acid with an alkaline solution in the absence of the ethoxylated 2-ethylhexanol. A stained fabric treated with an application of the linear alkyl benzene sulfonate solution may exhibit higher reflectance values than a fabric treated with the substantially similar solution.

To assess anti-redeposition performance, a white fabric may be added along with the stained fabrics during a treatment of the stained fabric with a given detergent. Treatment may comprise a laundry wash trial using the detergent. Reflectance (or percent reflectance) of the unwashed, non-stained white fabric may be observed prior to a laundering and then observed after the wash trial with a given stained fabric. Reflectance values closer to that observed for the unwashed, non-stained fabric may indicate that the detergent formulation is a suitable anti-redeposition agent. With respect to anti-redeposition properties, a white fabric included with the stained fabrics during a treatment of the disclosed solution may also exhibit higher reflection values. As an example, reflectance may be observed at 460 nanometers (460 nm).

As provided above, an application of the linear alkyl benzene sulfonate solution may comprise a laundry wash trial. An exemplary laundry wash trial may include the laundering of soiled fabrics in deionized water at 40 degrees Celsius (° C.) with a dosage of 0.4 percent weight by volume (% w/v) of the linear alkyl benzene sulfonate solution in a 25 gram per liter load. The wash trial may proceed in a tergotometer for example. The tergotometer may operate at 200 revolutions per minute (rpm) for a duration of 30 minutes. Upon completion of laundering, the fabric may be dried at room temperature.

The solutions described herein may be useful in the treatment of a number of stains on a given fabric. These stains may include a number of food or food related items such as soy sauce, curry spices, ketchup, spinach, red grape, Coca Cola™, apple juice, beef lard, blackberry juice, black currant juice, blood, blueberry juice, butterfat with colorant, carrot baby food, carrot juice, chocolate, chocolate cream, chocolate milk/carbon black, and egg yolks. Other stains to which the solution may be applied include makeup stains, lipstick stains, shoe polish, and used motor oil. Blood/milk/ink combination stains may also be treated. Certain pigment stains may also be treated with the disclosed solution. These pigment stains include pigment lanolin, pigment sebum, pigment vegetable fat, and pigment egg. In some aspects, the stained fabric may be a fabric having a stain type according to any one of a number of WFK stain types commercially available from Testgewebe GmbH or an EMPA stain type commercially available from of Switzerland standard stain type. For example, the stain may comprise soy sauce WFK 20V, pigment vegetable fat WFK 20PF, makeup WFK 20MU, curry WFK20U, pigment lanolin WFK 20C, ketchup WFK 20T, spinach WFK 20SP, Coca Cola™ WFK 20H, egg yolk WFK 20EG, lip stick WFK 20LS, pigment sebum WFK 20D, red grape WFK 20LIU, pigment egg WFK 20N, used motor oil WFK 20GM, shoe polish WFK 20S, or blood milk C EMPA 117. The white fabric may be a white fabric according to WFK Testgewebe GmbH WFK 20A.

Given the foregoing properties, the linear alkyl benzene sulfonate solution described herein may be useful in a detergent composition, particularly a laundry detergent composition. As an active detergent composition or laundry detergent composition, the linear alkyl benzene sulfonate solution may further comprise other hydrotropes and other surfactants, including anionic surfactants, cationic surfactants, amphoteric surfactants and/or amine oxides. The composition may further comprise additional detergent additives including (but not limited to) alkali, such as sodium hydroxide or potassium hydroxide, silicates, acids, solvents, other salts, perfumes, pH buffers, abrasives, imine bleach boosters; enzymes such as amylases, carbohydrases, cellulases, laccases, lipases, bleaching enzymes such as oxidases and peroxidases, proteases, pectate lyases and mannanases; source of peroxygen, additional soil anti-redeposition agents, preservatives, pacifiers, disinfectants, deodorants, colorants, corrosion inhibitors, foam regulators and rheology modifiers, such as polymers; in the usual amounts. However, to obtain a composition exhibiting an optimal performance and an excellent environmental profile, the presence of certain components is less desirable.

Definitions

It is to be understood that the terminology used herein is for the purpose of describing particular aspects only and is not intended to be limiting. As used in the specification and in the claims, the term "comprising" may include the aspects "consisting of" and "consisting essentially of." Unless defined otherwise, all technical and scientific terms used herein have the same meaning as commonly understood by one of ordinary skill in the art to which this disclosure belongs. In this specification and in the claims which follow, reference will be made to a number of terms which shall be defined herein. All publications mentioned herein are incorporated herein by reference to disclose and describe the methods and/or materials in connection with which the publications are cited.

As used in the specification and the appended claims, the singular forms "a," "an" and "the" include plural referents unless the context clearly dictates otherwise. Thus, for example, reference to "a polycarbonate" includes mixtures of two or more such polycarbonates. Furthermore, for example, reference to a filler includes mixtures of two or more such fillers.

Ranges can be expressed herein as from one value (first value) to another value (second value). When such a range is expressed, the range includes in some aspects one or both of the first value and the second value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" mean that the subsequently described event, condition, component, or circumstance may or may not occur, and that the description includes instances where said event or circumstance occurs and instances where it does not.

The term "alkyl" as used herein, may refer to a hydrocarbyl moiety which is straight or branched, saturated or unsaturated. Unless otherwise specified, alkyl moieties are preferably saturated or unsaturated with double bonds, preferably with less than two double bonds. Included in the term "alkyl" is the alkyl portion of acyl groups.

The term "linear" as used herein, with respect to LABS, indicates that the alkyl portions thereof contain less than about 30%, preferably less than about 20%, more preferably less than about 10% branched alkyl chains.

As used herein, "anti-re-deposition" may refer to the ability of a solution as a detergent to prevent the depositing of a liquid or solid stain when the staining liquid or solid is introduced to the wash bath.

"Hydrotrope" as used herein may refer to a substance or composition that improves the solubility of a surfactant in water. More specifically, hydrotrope may refer to systems containing high levels of builders or alkalinity.

As used herein, the term or phrase "effective," "effective amount," or "conditions effective to" refers to such amount or condition that is capable of performing the function or property for which an effective amount is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

Disclosed are component materials to be used to prepare disclosed compositions of the disclosure as well as the compositions themselves to be used within methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific aspect or combination of aspects of the methods of the disclosure.

References in the specification and concluding claims to parts by weight, of a particular element or component in a composition or article denotes the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included. For example if a particular element or component in a composition or article is said to have 8% weight, it is understood that this percentage is relation to a total compositional percentage of 100%.

Compounds disclosed herein are described using standard nomenclature. For example, any position not substituted by any indicated group is understood to have its valence filled by a bond as indicated, or a hydrogen atom. A dash ("—") that is not between two letters or symbols is used to indicate a point of attachment for a substituent. For example, —CHO is attached through carbon of the carbonyl group. Unless defined otherwise, technical and scientific terms used herein have the same meaning as is commonly understood by one of skill in the art to which this disclosure belongs.

The term "comparable" as used herein may refer to similarity between given resin compositions described herein. Comparable may be used to express that properties, or the quantified values of given properties, are similar to or commensurate with the properties of another.

As used herein, the term "substantially similar solution" refers to a solution that is substantially identical to the inventive composition by consisting essentially of substantially the same proportions and components as the inventive composition, but that does not include the indicated component (e.g., ethoxylated 2-ethylhexanol).

The term "transparency" as used herein may refer to a level of transmittance for a resin composition that is greater than 50%, including exemplary transmittance values of at least 60%, 70%, 80%, 85%, 90%, and 95%, or any range of transmittance values derived from the above exemplified values. In some examples, the resin composition may exhibit a transmittance value of greater than 85%. Transmittance may be measured for a disclosed resin composition according to ASTM method D1003.

The term "reflectance" as used herein refers to a ratio of the intensity of light or other radiation to that of the light or other radiation incident on a surface. Reflectance may be presented as a percentage and may be observed according to a number of standards known in the art including, for example, ASTM D 3050-07.

Aspects:

In various aspects, the present disclosure pertains to and includes at least the following aspects.

Aspect 1A. A method comprising: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is about 50% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 1B. A method consisting essentially of: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is about 50% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 1C. A method consisting of: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is about 50% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 2A. A method comprising: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 2B. A method comprising: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 2C. A method comprising: forming an alkaline solution; combining the alkaline solution with a portion of ethoxylated 2-ethylhexanol to provide an aqueous solution, wherein the ethoxylated 2-ethylhexanol comprises 7 moles ethylene oxide units; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the ethoxylated 2-ethylhexanol.

Aspect 3. The method of any of aspects 1A-2C, wherein an application of the alkyl benzene sulfonate solution to a stained fabric effects a reflectance observed at 460 nm of the stained fabric that is greater than a reflectance observed at 460 nm of the stained fabric that has been treated with the substantially similar solution.

Aspect 4. The method of aspect 3, wherein the stain comprises any one of the following stain types soy sauce WFK 20V, pigment vegetable fat WFK 20PF, makeup WFK 20MU, curry WFK 20U, pigment lanolin WFK 20C, spinach WFK 20SP, Coca Cola™ WFK 20H, egg yolk WFK, lipstick WFK 20LS, pigment sebum WFK 20D, red grape WFK 20LIU, pigment egg WFK 20N, used motor oil WFK GM, shoe polish WFK 20S, or blood-milk C EMPA 117 according to WFK Testgewebe GmbH.

Aspect 5. The method of any one of aspects 1A-4, wherein the alkaline solution is formed by dissolving an alkaline compound in a portion of water.

Aspect 6. The method of aspect 5, wherein the linear alkyl benzene sulfonic acid is added in a 1:1 molar ratio based on an amount of the alkaline compound.

Aspect 7. The method of any one of aspects 1A-6, wherein the alkaline solution is formed as a 1:1 ratio based upon the linear alkyl benzene sulfonic acid.

Aspect 8. The method of any one of aspects 1A-7, wherein the alkaline solution is formed by dissolving sodium hydroxide in a portion of water.

Aspect 9. The method of any one of aspects 1A-8, wherein the alkaline solution comprises a sodium hydroxide solution.

Aspect 10. The method of any one of aspects 1A-9, wherein the alkaline solution is formed by dissolving potassium hydroxide in a portion of water.

Aspect 11. The method of any one of aspects 1A-10, wherein the adding is performed under stirring.

Aspect 12. The method of any one of aspects 1A-11, wherein the linear alkyl benzene sulfonic acid comprises a C2 to C20 linear alkyl benzene sulfonic acid.

Aspect 13. The method of any one of aspects 1A-12, wherein the linear alkyl benzene sulfonic acid comprises a C12 linear alkyl benzene sulfonic acid.

Aspect 14. The method of any of aspects 1A-13, wherein the slowly adding step comprises dividing the linear alkyl benzene sulfonic acid into smaller portions and adding the smaller portions of linear alkyl benzene sulfonic acid to the aqueous solution.

Aspect 15. The method of any one of aspects 1A-14, wherein the linear alkyl benzene sulfonic acid is added in an amount so as to neutralize the aqueous solution.

Aspect 16. The method of any one of aspects 1A-15, wherein the ethoxylated 2-ethylhexanol comprises up to about 10 ethylene oxide units.

Aspect 17. The method of any one of aspects 1A-16, wherein the ethoxylated 2-ethylhexanol comprises seven ethylene-oxy units.

Aspect 18A. A composition formed by a method comprising: forming caustic soda solution; combining the caustic soda solution with a portion of a ethoxylated 2-ethylhexanol to provide an aqueous solution; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the caustic soda solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the 2-ethylhexanol ethoxylated.

Aspect 18B. A composition formed by a method consisting essentially of: forming caustic soda solution; combining the caustic soda solution with a portion of a ethoxylated 2-ethylhexanol to provide an aqueous solution; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the caustic soda solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the 2-ethylhexanol ethoxylated.

Aspect 18C. A composition formed by a method consisting of: forming caustic soda solution; combining the caustic soda solution with a portion of a ethoxylated 2-ethylhexanol to provide an aqueous solution; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the caustic soda solution and the linear alkyl benzene sulfonic acid in the absence of the ethoxylated 2-ethylhexanol, and wherein the linear alkyl benzene sulfonate solution exhibits values for surface tension and foaming properties within about 6% of the values for surface tension and foaming of the substantially similar solution in the absence of the 2-ethylhexanol ethoxylated.

Aspect 19. The composition of any one of aspects 18A-18C, wherein the ethoxylated 2-ethylhexanol comprises seven moles ethylene oxide units.

Aspect 20A. An aqueous sodium alkyl benzene sulfonate solution comprising: an alkaline solution; a portion of ethoxylated 2-ethylhexanol; and a linear alkyl benzene sulfonic acid, wherein the aqueous sodium alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the alkyl benzene sulfonate solution exhibits values for surface tension and foaming properties within about 5% of the values for surface tension and foaming of the substantially similar solution in the absence of the ethoxylated 2-ethylhexanol; and wherein an application of the alkyl benzene sulfonate solution to a stained fabric results in a reflectance at 460 nm at the stained fabric that is greater than a reflectance observed at 460 nm at the stained fabric at which the substantially similar solution has been applied.

Aspect 20B. An aqueous sodium alkyl benzene sulfonate solution consisting essentially of: an alkaline solution; a portion of ethoxylated 2-ethylhexanol; and a linear alkyl benzene sulfonic acid, wherein the aqueous sodium alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the alkyl benzene sulfonate solution exhibits values for surface tension and foaming properties within about 5% of the values for surface tension and foaming of the substantially similar solution in the absence of the ethoxylated 2-ethylhexanol; and wherein an application of the alkyl benzene sulfonate solution to a stained fabric results in a reflectance at 460 nm at the stained fabric that is greater than a reflectance observed at 460 nm at the stained fabric at which the substantially similar solution has been applied.

Aspect 20C. An aqueous sodium alkyl benzene sulfonate solution consisting of: an alkaline solution; a portion of ethoxylated 2-ethylhexanol; and a linear alkyl benzene sulfonic acid, wherein the aqueous sodium alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the alkyl benzene sulfonate solution exhibits values for surface tension and foaming properties within about 5% of the values for surface tension and foaming of the substantially similar solution in the absence of the ethoxylated 2-ethylhexanol; and wherein an application of the alkyl benzene sulfonate solution to a stained fabric results in a reflectance at 460 nm at the stained fabric that is greater than a reflectance observed at 460 nm at the stained fabric at which the substantially similar solution has been applied.

Aspect 21. The aqueous sodium alkyl benzene sulfonate solution of any of aspects 20A-20C, wherein the ethoxylated 2-ethylhexanol comprises seven moles ethylene-oxy units.

Without further elaboration, it is believed that one skilled in the art can, using the description herein, utilize the present disclosure. The following examples are included to provide addition guidance to those skilled in the art of practicing the claimed disclosure. The examples provided are merely representative of the work and contribute to the teaching of the present disclosure. Accordingly, these examples are not intended to limit the disclosure in any manner.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior disclosure. Further, the dates of publication provided herein can be different from the actual publication dates, which can require independent confirmation.

EXAMPLES

The following examples are put forth so as to provide those of ordinary skill in the art with a complete disclosure and description of how the methods, devices, and systems disclosed and claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in degrees Celsius (° C.) or is at ambient temperature, and pressure is at or near atmospheric.

Inventive and comparative solutions comprising linear alkyl benzene sulfonic acid neutralized with sodium hydroxide. Inventive sample LABS001 was prepared by neutralizing, or mixing, linear alkyl benzene sulfonic acid with sodium hydroxide in the presence of ethoxylated 2-ethylhexanol 7EO as a hydrotrope. Comparative example LABS002 were prepared by neutralizing linear alkyl benzene sulfonic acid with a sodium hydroxide solution. Physically, the inventive sample LABS001 was free flowing and readily mixed during preparation of the sample.

Values for viscosity, surface tension, and foaming were obtained for LABS001 and LABS002. Viscosity was determined according to ASTM D 2983-15 at 20° C. using a Brookfield viscometer. Static and dynamic surface tensions were also obtained according to ASTM D 1331-14 using a Surface Tensiometer Lauda TD3 and Lauda MPT C for 0.2% aqueous (aq.) solutions at 20° C. Foaming was measured according to ASTM D113-07 at 20° C. for 0 minutes and 5 minutes. A Draves Skein wetting time was also obtained as the wetting ability of a foam solution according to ASTM D2281-10 at 20° C. Table 1 provides the values for viscosity, surface tensions, foaming, and wetting time. It was observed that the presence of ethoxylated 2-ethylhexanol did not affect surface tension or foaming.

TABLE 1

Viscosity, surface tension, foaming and wetting time of inventive (LABS001) and comparative (LABS002) linear alkyl benzene sulfonate solutions.

| Properties | LABS 001 | LABS 002 | % difference |
|---|---|---|---|
| Viscosity 20° C. (centipoise, cP) | 3050 | 6200 | 103.3% |
| Static surface tension 0.2% aq., 20° C. (milliNewtons per meter, mN/m) | 35.3 | 34.3 | 2.9% |
| Dynamic surface tension 0.2% aq., 20° C. (mN/m) | 46.3 | 45.3 | 2.2% |
| Foam 0.2% aq., 20° C. at 0 min. (centimeters, cm) | 16.3 | 16.9 | 3.7% |
| Foam 0.2% aq. 20° C. at 5 min. (cm) | 15.5 | 15.4 | 0.6% |
| Draves Skein wetting time 20° C. (seconds, sec) | 10.37 | 9.02 | 13% |

As shown in table 1, LABS002 in the absence of the hydrotrope ethoxylated 2-ethylhexanol exhibited a viscosity more than two times that of LABS001 which included ethoxylated 2-ethylhexanol. However, there was no significant difference in surface tension and foaming.

Samples were also evaluated for detergency and anti-redeposition properties. Detergency may refer to the removal of liquid or solid substances (i.e., stains) from a solid surface brought in contact with the sample. Laundry wash trials were conducted using a tergotometer and deionized water at 40° C. The fabric used for the laundry wash trials was a polyester cotton blend (70:30, cotton:polyester). The wash trials were performed at 200 revolutions per minute (rpm) for 30 minutes with a load of 25 grams per liter (g/L) and a dosage of 0.4% weight by volume. The laundered samples were dried at room temperature. Reflectance was obtained at each samples of laundered fabric according to their stain types. Results are presented in Table. 2.

TABLE 2

Reflectance for LABS001 and LABS002 Laundered Samples after Wash Trial

| Stain type | Reflectance @ 460 nm | |
|---|---|---|
| | LABS 001 | LABS 002 |
| Soy sauce WFK 20V | 76.1 | 76.0 |
| Pigment Veg fat WFK 20PF | 45.0 | 42.7 |
| Make up WFK 20MU | 70.7 | 69.1 |
| Curry WFK 20U | 65.3 | 64.2 |
| Pigment Lanolin WFK 20C | 39.9 | 38.0 |
| Ketchup WFK 20T | 75.7 | 75.8 |
| Spinach WFK 20SP | 76.4 | 74.8 |
| Coca cola WFK 20H | 70.6 | 68.0 |
| Egg Yolk WFK 20EG | 72.5 | 71.0 |
| Lip stick WFK 20LS | 28.3 | 29.2 |
| Pigment Sebum WFK 20D | 45.2 | 45.1 |
| Red grape WFK 20LIU | 70.6 | 69.6 |
| Pigment Egg WFK 20N | 70.0 | 69.4 |
| Used motor oil WFK 20GM | 37.8 | 36.5 |
| Shoe polish WFK 20S | 12.5 | 12.1 |
| Pigment Olive oil WFK 20B | 38.8 | 39.6 |
| Chocolate WFK 20Z | 69.0 | 69.0 |
| Blood, milk, C EMPA 117 | 46.5 | 46.3 |
| White fabric WFK 20A (Anti redeposition) | 77.9 | 77.2 |

For every stain type except, ketchup (WFK 20T), pigment olive oil (WFK 20B), and chocolate (WFK 20Z), the LABS001 treated sample exhibited a higher reflectance. With respect to anti-redeposition properties, the LABS001 treated white fabric exhibited a higher reflectance (77.9 for LABS001 compared to 77.2 LABS002). Thus, the LABS001 was better able to prevent the redeposition of stains on the white fabric when compared to the LABS002 sample.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

The patentable scope of the disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An aqueous sodium alkyl benzene sulfonate solution comprising:
   an alkaline solution;
   0.05 wt. % of ethoxylated 2-ethylhexanol; and a linear alkyl benzene sulfonic acid, wherein the aqueous sodium alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the alkyl benzene sulfonate solution exhibits values for surface tension and foaming properties within about 5% of the values for surface tension and foaming of the substantially similar solution in the absence of the ethoxylated 2-ethylhexanol; and wherein an application of the alkyl benzene sulfonate solution to a stained fabric results in a reflectance at 460 nm at the stained fabric that is greater than a reflectance observed at 460 nm at the stained fabric at which the substantially similar solution has been applied.

2. The aqueous sodium alkyl benzene sulfonate solution of claim 1, wherein the ethoxylated 2-ethylhexanol comprises seven moles of ethylene oxide units.

3. The aqueous sodium alkyl benzene sulfonate solution of claim 1, wherein the alkaline solution has a 1:1 molar ratio based upon the linear alkyl benzene sulfonic acid.

4. The aqueous sodium alkyl benzene sulfonate solution of claim 1, wherein the alkaline solution comprises a sodium hydroxide solution.

5. The aqueous sodium alkyl benzene sulfonate solution of claim 1, wherein the linear alkyl benzene sulfonic acid comprises a C2 to C20 linear alkyl benzene sulfonic acid.

6. The aqueous sodium alkyl benzene sulfonate solution of claim 1, wherein the linear alkyl benzene sulfonic acid comprises a C12 linear alkyl benzene sulfonic acid.

7. The aqueous sodium alkyl benzene sulfonate solution of claim 1, wherein the linear alkyl benzene sulfonic acid is present in an amount to neutralize the aqueous solution.

8. The aqueous sodium alkyl benzene sulfonate solution of claim 1, wherein the ethoxylated 2-ethylhexanol comprises up to about 10 ethylene oxide units.

9. A method of preparing the aqueous sodium alkyl benzene sulfonate solution of claim 1 comprising: forming an alkaline solution; combining the alkaline solution with the ethoxylated 2-ethylhexanol to provide an aqueous solution; and slowly adding the linear alkyl benzene sulfonic acid to the aqueous solution to provide the aqueous sodium alkyl benzene sulfonate solution.

10. The method of claim 9, wherein an application of the aqueous sodium alkyl benzene sulfonate solution to a stained fabric effects a reflectance observed at 460 nm of the stained fabric that is greater than a reflectance observed at 460 nm of the stained fabric that has been treated with the substantially similar solution.

11. An aqueous sodium alkyl benzene sulfonate solution consisting of:
   an alkaline solution;
   ethoxylated 2-ethylhexanol; and a linear alkyl benzene sulfonic acid, wherein the aqueous sodium alkyl benzene sulfonate solution exhibits a viscosity that is at least about 40% less than the viscosity of a substantially similar solution, wherein the substantially similar solution comprises the alkaline solution and the linear alkyl benzene sulfonic acid in the absence of the ethoxylated 2-ethylhexanol, and wherein the alkyl benzene sulfonate solution exhibits values for surface tension and foaming properties within about 5% of the values for surface tension and foaming of the substantially similar solution in the absence of the ethoxylated 2-ethylhexanol; and wherein an application of the alkyl benzene sulfonate solution to a stained fabric results in a reflectance at 460 nm at the stained fabric that is greater than a reflectance observed at 460 nm at the stained fabric at which the substantially similar solution has been applied.

12. A composition formed by a method comprising: forming caustic soda solution; combining the caustic soda solution with 0.05 wt. % of an ethoxylated 2-ethylhexanol to provide an aqueous solution; and slowly adding linear alkyl benzene sulfonic acid to the aqueous solution to provide a linear alkyl benzene sulfonate solution wherein the linear alkyl benzene sulfonate solution exhibits a viscosity that is at least about 40% less than the viscosity of a substantially similar solution, wherein the substantially similar solution comprises the caustic soda solution and the linear alkyl benzene sulfonic acid in the absence of the ethoxylated 2-ethylhexanol, and wherein the linear alkyl benzene sulfonate solution exhibits values for surface tension and foaming properties within about 5% of the values for surface tension and foaming of the substantially similar solution in the absence of the ethoxylated 2-ethylhexanol; wherein the ethoxylated 2-ethylhexanol comprises seven moles ethylene oxide units.

* * * * *